US00PP12421P2

(12) United States Plant Patent

Yoshida et al.

(10) Patent No.: US PP12,421 P2

(45) Date of Patent: Feb. 26, 2002

(54) APPLE TREE 'KOTARO'

(75) Inventors: Yoshio Yoshida, Ebetsu; Shichiro Tsuchiya, Ryugasaki; Junichi Soejima, Morioka; Tadayuki Haniuda, Nagano; Tetsuro Sanada, Morioka; Yoshiki Kashimura, Tsukuba; Tetsuo Masuda, Morioka; Hideo Bessho, Yamanashi; Sadao Komori, Ishigaki; Yuji Ito, Ibaraki; Kazuyuki Abe, Morioka; Nobuhiro Kotoda, Morioka; Hidenori Kato, Morioka, all of (JP)

(73) Assignee: National Institute of Fruit Tree Science Ministry of Agriculture Forestry and Fisheries, Ibaraki (JP)

( * ) Notice: Subject to any disclaimer, the term of this patent is extended or adjusted under 35 U.S.C. 154(b) by 0 days.

(21) Appl. No.: 09/270,840

(22) Filed: Mar. 18, 1999

(30) Foreign Application Priority Data

Apr. 8, 1998 (JP) ..... 10857

(51) Int. Cl.[7] ..... A01H 5/00

(52) U.S. Cl. ..... Plt./161

(58) Field of Search ..... Plt./161

(56) References Cited

U.S. PATENT DOCUMENTS

PP7,106 P * 1/1990 Hatakoshi ..... Plt./161

OTHER PUBLICATIONS

GTITM UPOVROM Citation for 'Ringo Morioka 56GO' as per JP 10857; Apr. 9, 1998.*

* cited by examiner

*Primary Examiner*—Bruce R. Campell
*Assistant Examiner*—Kent L. Bell
(74) *Attorney, Agent, or Firm*—Armstrong, Westerman, Hattori, McLeland & Naughton, LLP

(57) ABSTRACT

Disclosed is an apple tree having a strong vigor, rounded and serrate leaves, exhibiting excellent resistance to Alternaria blotch, bearing a medium size fruit maturing mid-season and having high productivity with little early fruit drop and preharvest fruit drop. The fruit has a rounded shape with good appearance, having solid, deep red colored skin and having relatively good storage quality, which is slightly inferior to the seed parent. The flesh of the fruit is yellowish white, juicy and firm, and further, has a moderate sweetness, weak sourness and an aroma, thereby providing a good sweet-sour balance, and an excellent eating quality.

8 Drawing Sheets

BACKGROUND OF THE VARIETY

The present invention relates to a new and distinctive variety of apple tree belonging to a medium-maturing apple cultivar, and more particularly, relates to an apple variety having high quality and high disease resistance for eating raw and for processing.

Regarding medium-maturing apple varieties, although 'Jonathan' and 'Starking Delicious' were widely cultivated in the past, they were not popular due to their taste and poor storage quality, and there are no main medium-maturing apple varieties now known to us. Thus it was necessary to breed a main medium-maturing apple variety immediately.

Accordingly, the present breeders crossed 'Hatsuaki', which is an excellent variety for both eating raw and for processing, with 'Fuji', which is a main economical variety, to obtain excellent medium-maturing apple varieties having good fruit quality and high productivity. Namely, the purpose of the invention is to avoid russet on fruit surface and to improve storage quality of the medium-maturing variety 'Hatsuaki' and to breed a new and distinct variety of medium-maturing apple variety having excellent disease resistance for eating raw and for processing.

ORIGIN AND ASEXUAL REPRODUCTION OF THE VARIETY

To produce the new variety, the breeders crossed 'Fuji', which had been cultivated at the Morioka branch of the Fruit Tree Research Station (currently the Apple Research Center, the National Institute of Fruit Tree Science), in Japan, and 'Hatsuaki', in 1976, and obtained seeds. The seeds obtained were utilized for sowing and raising seedlings at said branch, in 1977, and the resulting seedlings were then grafted on 'M.27', the most dwarfing rootstock, to accelerate bearing, in 1978, and 127 individuals were set in 1980.

The trees bore fruit in 1983 and one was selected in the primary selection as a good medium-maturing individdual in 1986. The present invention is directed to an apple tree 'Kotaro', which is one individual from amount 127 individuals derived from the cross 'Fuji' (♀) (the seed parent) and 'Hatsuaki' (♂) (the pollen parent), and was given an individual number "601" during testing. The tree was selected as a favorable line of trees, which have a line name Ringo Morioka 56 Go, have been provided for local adaptability tests since 1991, and were examined to determine the various characteristics thereof, over a period of seven years from April 1991 to March 1998. As a result, it was found that, for example, fruit of the trees had the desired characteristics, such as quality, storage quality and yield, as a medium-maturing apple variety, and the tree was distinguishable from the parent varieties, 'Fuji' and 'Hatsuaki', as well as a control variety 'Jonagold'. Accordingly, the breeders denominated this variety as 'Kotaro', in accordance with this invention. The genus and species of the tree is *Malus*× *domestica*.

Of the varieties, 'Fuji' is a variety generated from a cross between 'Ralls Janet' and 'Delicious'.

Of the varieties, 'Hatsuaki' is a variety generated from a cross between 'Jonathan' and 'Golden Delicious'.

The breeders asexually reproduced this new and distinctive variety of apple tree 'Kotaro', by grafting on rootstock 'M.27' (U.S. Plant Pat. No. 3,793), at a number of Fruit Tree Research Stations in Morioka City, Iwate prefecture, Japan, and confirmed the homogeneity and stability of 'Kotaro' according to the present invention. The instant plant retains its distinctive characteristics and reproduces true to type in successive generations.

Of the above varieties, only M.27 is known to us as having been patented in the United States.

An application for this new variety of apple tree, 'Kotaro' under the Seeds and Seedlings Law of Japan, was filed on Apr. 9, 1998, under the filing number 10857.

The original tree of this apple tree is held at the Apple Research Center of the National Institute of Fruit Tree Science, Ministry of Agriculture, Forestry and Fisheries, residing at 92 Nabeyashiki, Shimokuriyagawa, Morioka City, Japan.

SUMMARY OF VARIETY

This new variety of apple tree is vigorous and spreading, and many spurs and axillary buds are formed.

The leaves of the tree are rounded and serrated.

At Morioka City, Iwate prefecture, Japan, the trees have a flowering time around May 21st which is about 4 days later than that of 'Jonagold' and 'Fuji'. The number of flowers per cluster is about 4–6 and flower is single and number of petals per a flower is 5. The flower color opened is white and unopened it is deep pink. The size of the flower is small, the same as that of 'Ralls Janet'. The amount of pollen is high and the present variety is self-unfruitful (the variety is not fructified by self-pollination). As the type of S gene of the present variety is (S3, Sf), though it is cross-incompatible with 'Akibae', 'Shinsekai' and 'Gunmameigetu' (unpatented to our knowledge), the cross-compatibility with common cultivars except the above varieties is high.

Early fruit drop and preharvest drop of fruit are few and the present variety shows high productivity. Of the main diseases, the tree is resistant to Alternaria blotch, but is susceptible to scab. It has not been recognized so far that any disease or insect except for the above, is significant.

The ripening of the present fruit occurs in late October at Morioka, as same as that of 'Jonagold'. The size of the fruit is medium and averages about 250 g, and is slightly smaller than that of 'Fuji', and the shape of the fruit is rounded. The type of over color of skin of the fruit is red-purple (60A by R.H.S.) and it has a good appearance and has a tendency to have a silvery mottle. The occurrence of russet on the surface of the fruit is slight.

The flesh of the present fruit contains about 14–15% Brix of total sugar, and about 0.4 g/100 ml of malic acid, and further the flesh is firm and juicy, and has a moderate sweetness and weak sourness, an aroma, provides a good sweet-sour balance and has excellent eating quality. The storage quality of the fruit is relatively good, but inferior to that of 'Fuji', and is about 25 days at room condition and about 70 days in cold storage.

Compared with the seed parent, 'Fuji', the present variety is distinguishable in that ripening of the fruit is earlier by about 2 weeks than that of 'Fuji', the type of over color of the skin of the present variety is solid, i.e. not striped, whereas that of 'Fuji' is striped, the fruit of the present variety does not have tendency to an inclination of the axis, as does 'Fuji', and the flesh of the present variety has a medium aroma, whereas that of 'Fuji' is weak.

Compared with the pollen parent, 'Hatsuaki', the present variety is distinguishable in that the ripening of the fruit is later by about 25 days than that of 'Hatsuaki', the flesh of the present variety is firm, acidity is weak and the flesh has a moderate sweet-mellow aroma.

Compared with 'Jonagold', the present variety is clearly distinguishable in that the leaves and the fruit of the present variety are smaller than those of 'Jonagold', the flesh of the present variety is firm, acidity of that is weak, the flesh has an aromatic flavor, and the greasiness of the peel after storage is weak.

The color references are made to The Royal Horticultural Society Colour Chart (R.H.S.) except where general terms of ordinary significance are used.

DESCRIPTION OF THE VARIETY

Figure 1:
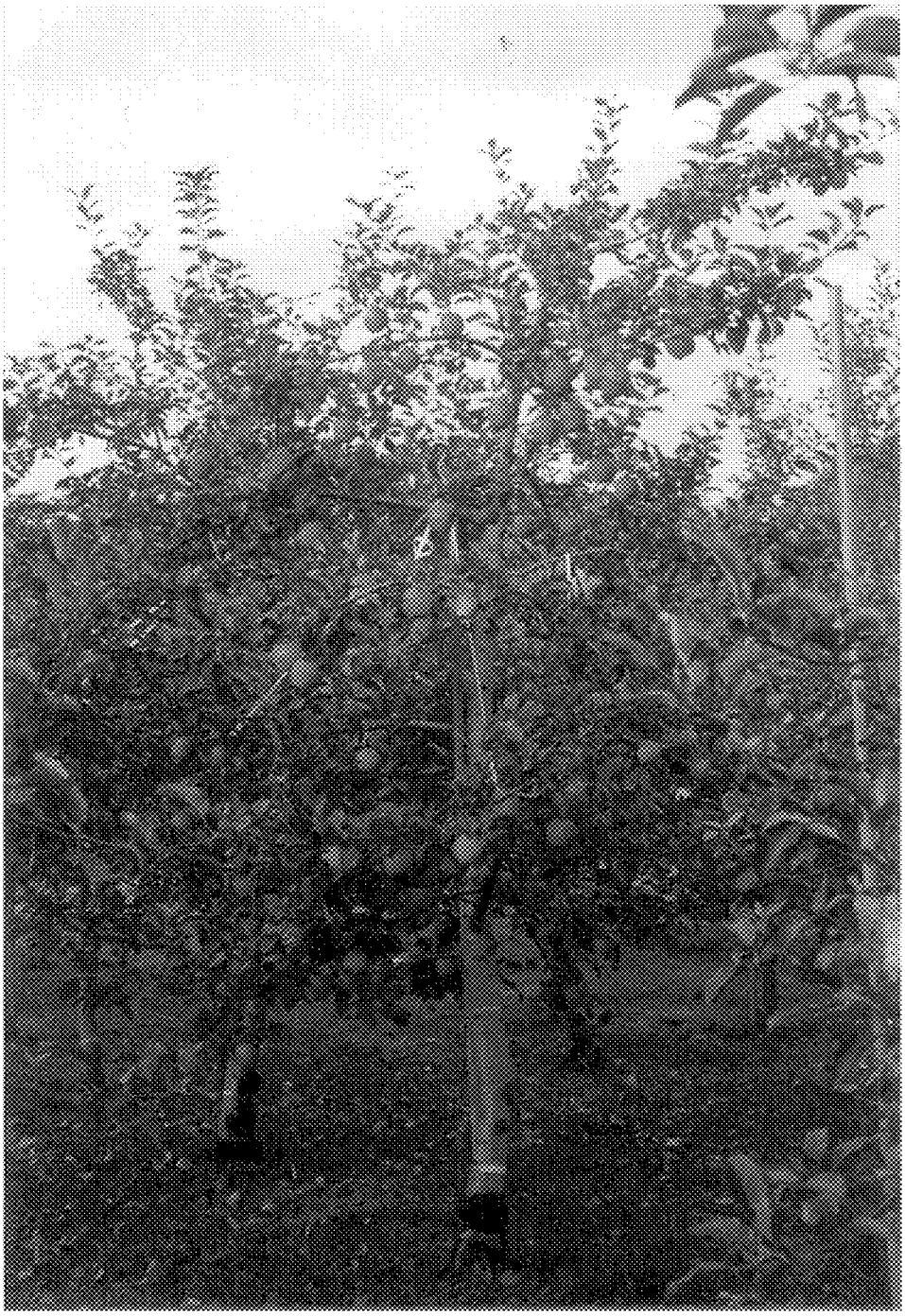
FIG. 1 is a photograph of the tree shape of the new variety of apple tree grafted on 'M.26' (10 years old)
Figure 2:
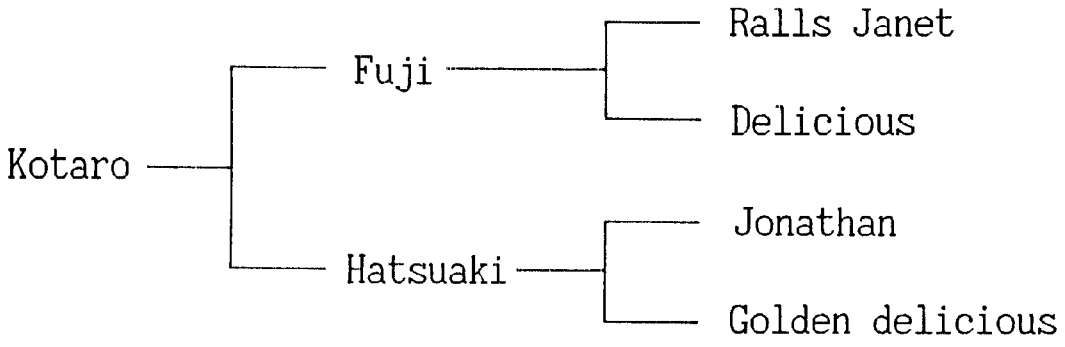
FIG. 2 gives the pedigree of the new and distinct variety of the apple tree 'Kotaro'.
Figure 3:
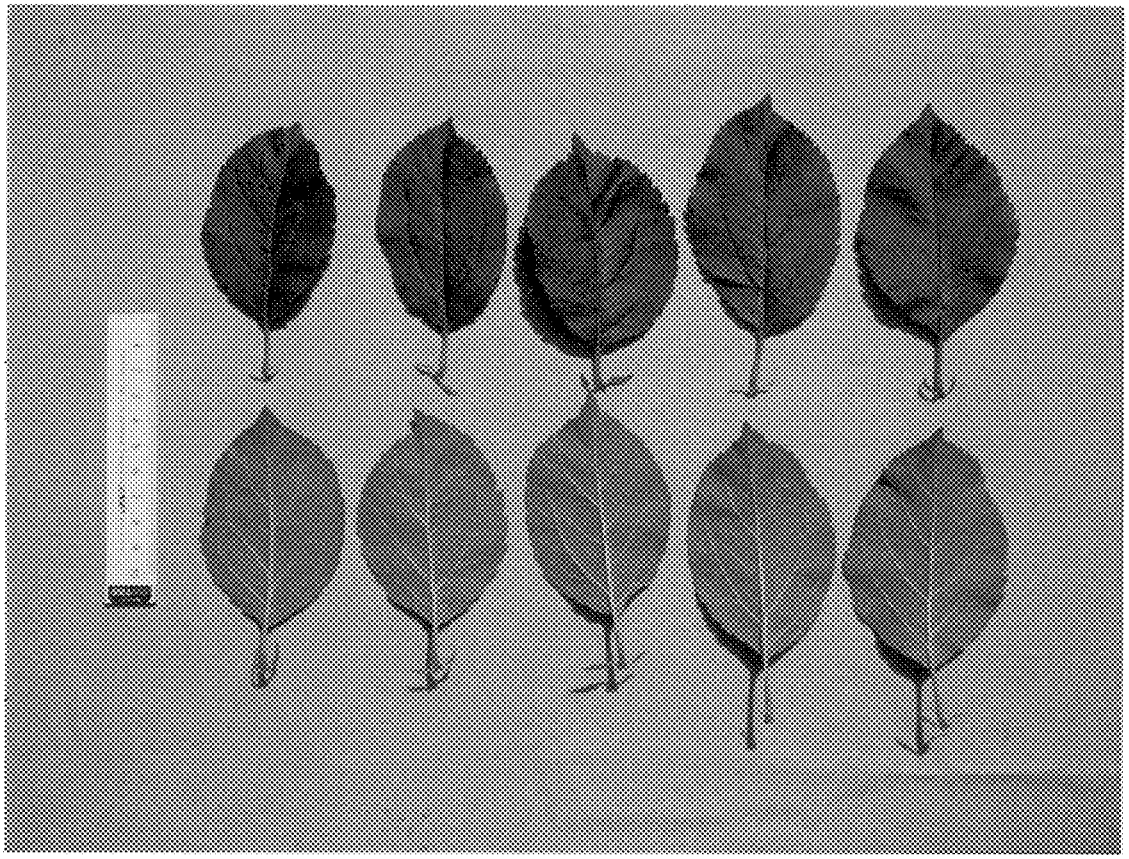
FIG. 3 is a photograph of adult leaves (upper and under side) of the new variety of apple tree.
Figure 4:
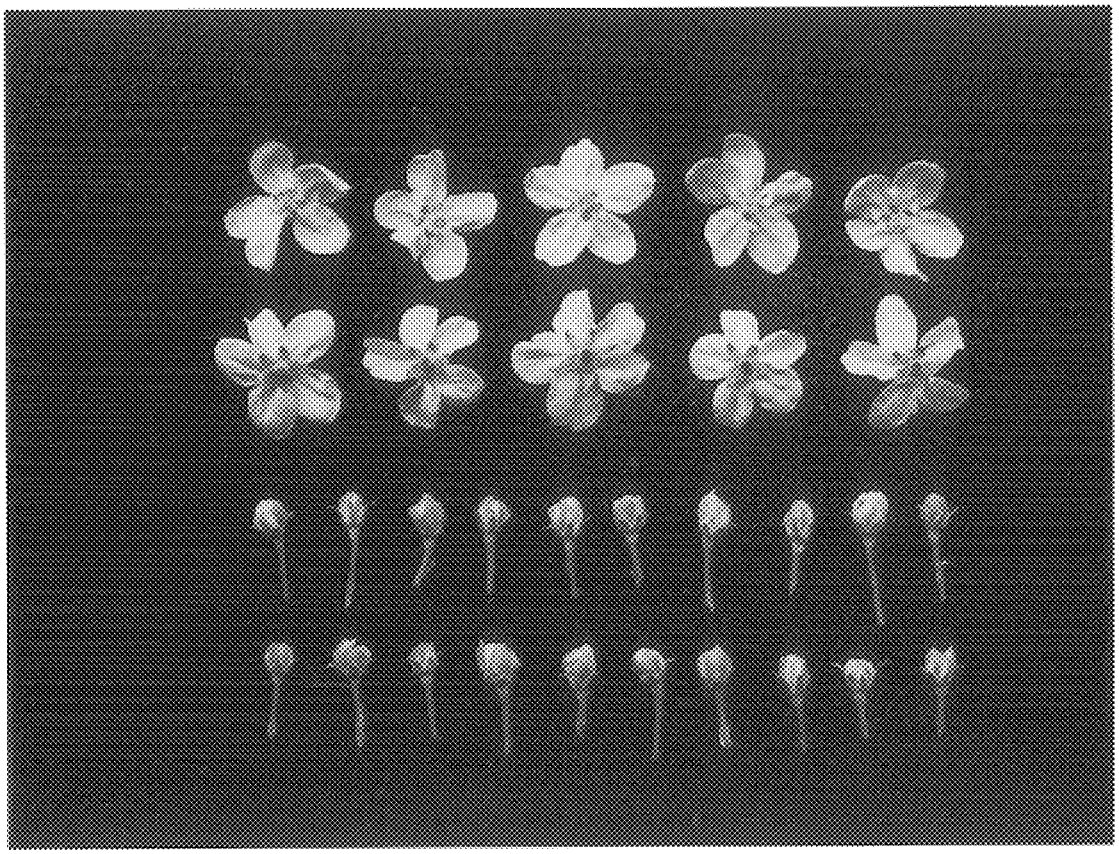
FIG. 4 is a photograph of the flowers (opened and unopened) of the new variety of apple tree.
Figure 5:
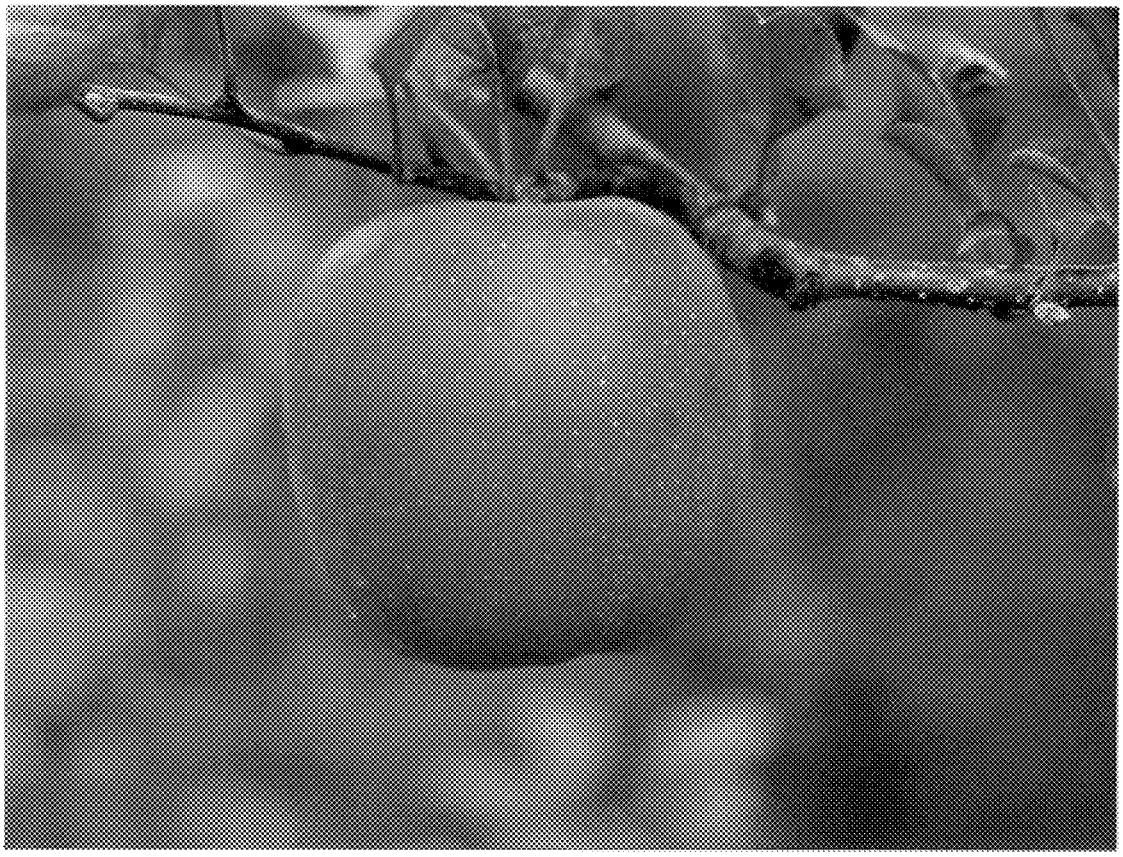
FIG. 5 is a photograph of fruits on the tree of the new variety of apple tree.
Figure 6:
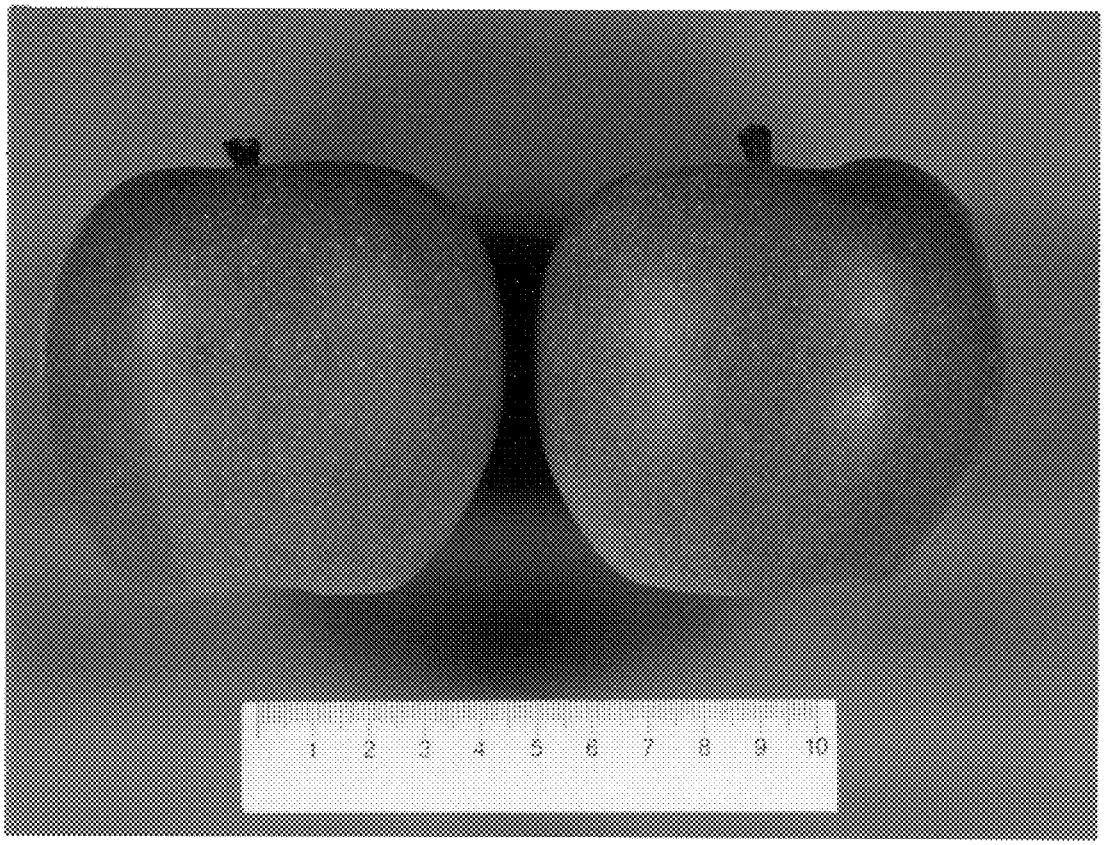
FIG. 6 is a photograph of a side view of the fruit of the new variety of apple tree.
Figure 7:
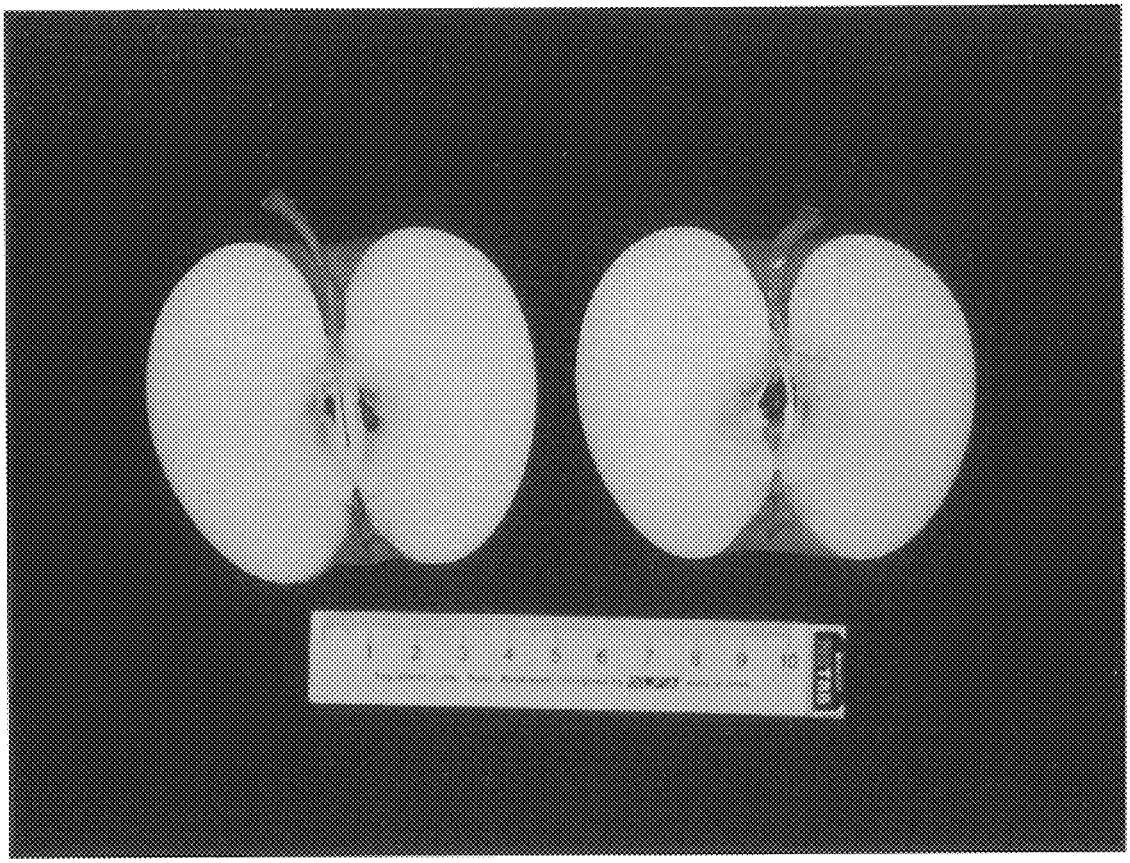
FIG. 7 is a photograph of a longitudinal-sectional view of the fruit of the new variety of apple tree; and, FIG. 8 is a photograph of a cross-sectional view of the fruit of the new variety of apple tree.
Figure 8:
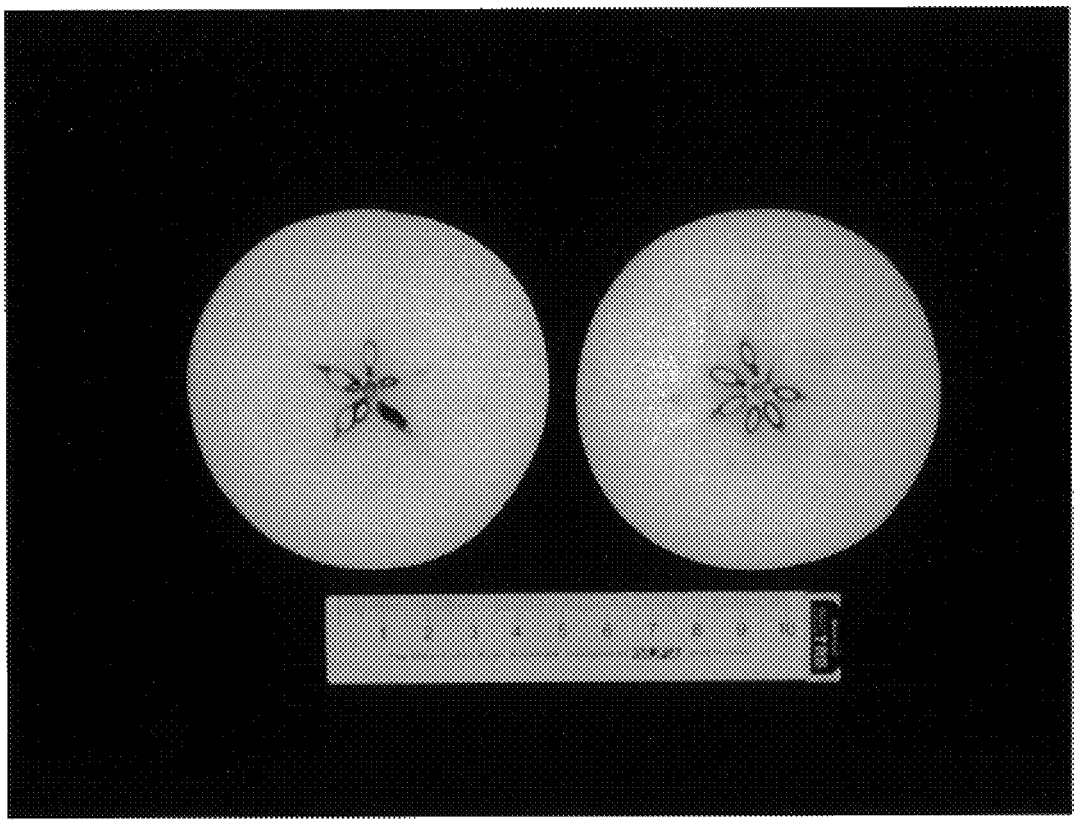

The characteristics of the new and distinct variety of apple tree 'Kotaro' are as follows (10-year-old tree in Morioka City, Iwate prefecture, Japan):

Tree:

*Habit of branches.*—Spreading, same as 'Jonagold' and 'Fuji'.

*Size.*—Large, larger than 'Jonagold' and the same as 'Fuji' (the observed tree height is 364 cm, however, this is not the natural tree height, as the top of the tree was cut to facilitate work).

*Trunk diameter.*—11.4 cm at 30 cm above soil level.

*Shoot length.*—39.3 cm.

*Time to produce a fruit-bearing tree.*—4 years in Morioka City, Iwata prefecture, Japan.

*Crotch angles.*—64.5°.

*Length of four-year-old* branch.—112 cm.

*Diameter of the middle of four-year-old branch.*—11.1 mm.

*Texture.*—Slightly rough.

*Coloration.*—Gray-brown (199D).

*Diameter* (*one-year-old shoot*).—Medium (4.0 mm).

*Length of internode* (*one-year-old shoot*).—Short (about 2.4 cm).

*Size of lenticels* (*one-year-old shoot*).—Length 1.75 mm and width 0.55 mm (larger than 'Jonagold' and much larger than 'Fuji').

*Number of lenticels* (*one-year-old shoot*).—10.7/cm$^2$ (numerous, same as 'Fuji' and many more than 'Jonagold').
*Pubescence of shoot.*—Moderately dense.
*Bearing habit of fruit.*—On spur.

Leaf:
*Shape of leaf blade.*—Elliptic.
*Leaf margin.*—Serrate.
*Size of leaf* (*length*).—Medium (length about 9.2 cm, width about 6.0 cm), shorter than 'Jonagold' and the same as 'Fuji'.
*Leaf apex.*—Acuminate.
*Leaf base.*—Cuneate.
*Venation pattern.*—Venose.
*Color of Leaf.*—Upper leaf green (133A) and under leaf green (138C) (same as 'Jonagold' and 'Fuji').
*Pubescence.*—Sparse.
*Shape of stipules.*—Sickle.
*Size of stipules.*—Length 10.2 mm and width 1.6 mm.
*Color of stipules.*—Upper surface green (133A) and under surface green (138C).
*Size of petiole.*—Length 21.0 mm, thickness 1.8 mm.
*Color of petiole.*—Upper part yellow-green (150D) and base part red (42D).

Flowers:
*Shaped and size of flower bud.*—Ovoid, length 12.9 mm and diameter 11.9 mm.
*Color of flower bud.*—Red-purple (58B to 65D).
*Number of flowers* (*per cluster*).—Medium (4 to 6).
*Size* (*open flower*).—Diameter 46 mm.
*Color* (*unopen flower*).—Deep pink.
*Shape of petal.*—Round, apex shape obtuse and base shape mucronate.
*Leaf margin.*—Entire.
*Texture of petal.*—Soft.
*Size of petal.*—Length 21.8 mm and width 16.8 mm.
*Color of petal.*—Upper surface red-purple (69D) and under surface red-purple (63D to 65D).
*Number of petals.*—Medium (5).
*Number of stamens.*—Medium.
*Color of anthers.*—Light yellow.
*Number of sepals.*—5.
*Size of sepals.*—Length 9.4 mm and width 3.9 mm.
*Shape of sepals.*—Sharp pointed, apex shape acute, bases linked together.
*Color of sepals.*—Upper surface green (139D) and under surface green (138D).
*Amount of pollen.*—High, same as 'Fuji'.
*Color of pollen.*—Yellow (7A).

Fruit:
*Shape.*—Round, same as 'Jonagold' and 'Fuji'.
*Crowning at eye end.*—Weak.
*Aperture of eye.*—Closed.
*Depth of basin* (*eye end*).—Medium (9 mm).
*Breadth of basin* (*eye end*).—Broad (34 mm).
*Depth of stalk cavity.*—Medium (17 mm).
*Diameter of stalk cavity.*—Medium (35 mm).
*Size.*—Length 75 mm and diameter 80 mm.
*Weight.*—Medium (about 250 g), smaller than 'Jonagold' and 'Fuji'.
*Type of ground color.*—Yellow (5C), same as 'Jonagold' and 'Fuji'.
*Type of over color of skin.*—Red-purple (60A), same as 'Jonagold'.
*Form of over color of skin.*—Solid (undistinguished stripe), unlike that of 'Jonagold' and 'Fuji'.
*Amount of over color of skin.*—90% (more than 'Jonagold' and 'Fuji').
*Position of russet.*—Around cavity, as opposed to on cheeks for 'Jonagold' and 'Fuji'.
*Amount of russet.*—Less than 1% (same as 'Fuji').
*Raised russet lenticels.*—Absent, same as 'Jonagold' and 'Fuji'.
*Diameter of lenticels.*—0.7 mm.
*Number of lenticels.*—4.8/cm$^2$, much more than 'Jonagold' and 'Fuji'.
*Amount of silvery mottle of skin.*—20%, same as 'Fuji', even though absent in 'Jonagold'.
*Luster of skin color.*—Not shiny.
*Greasiness of skin.*—Weak.
*Bloom of skin.*—Present.
*Cracking tendency of skin.*—None.
*Surface texture of skin.*—Smooth.
*Length of stalk.*—Medium (2.6 cm).
*Diameter of stalk.*—Medium (2.0 mm).
*Distinct swelling at end of stalk.*—None.
*Shape of core.*—Flat round, as opposed to conical with 'Jonagold' and 'Fuji'.
*Size of core.*—Medium (length 32.3 mm and diameter 38.1 mm).
*Number of core cells.*—Medium (5 core cells).
*Color of flesh.*—Yellow (11D), same as 'Jonagold' and 'Fuji'.
*Bruising of flesh.*—Difficult.
*Browning of flesh.*—Medium.
*Firmness of flesh.*—Firm.
*Texture of flesh.*—Fine, finer than 'Fuji'.
*Water core.*—None or weak.
*Sweetness of flesh.*—Medium (Brix about 14–15%), same as 'Jonagold' and 'Fuji'.
*Acidity of flesh.*—Weak (about 0.4 g/100 ml).
*Astringency of flesh.*—None.
*Aroma of flesh.*—Medium.
*Juiciness of flesh.*—Very juicy, same as 'Jonagold' and 'Fuji'.

Seed:
*Total amount of fully developed seeds.*—Medium (about 7.4 per apple).
*Total amount of perfect seeds.*—About 7.4 per apple.
*Shape.*—Ovoid.
*Size.*—Medium (length 9.4 mm and width 4.5 mm).
*Color.*—Gray-orange (166A).

Physiological and ecological characteristics:
*Date of germination.*—Late (April 10th at Morioka City, Iwate prefecture, Japan), later than 'Jonagold' and 'Fuji'.
*Season of flowering.*—Late (first day of bloom May 16th, last day of bloom May 25th, day of full bloom May 21st, at Morioka City, Iwate prefecture, Japan), later than 'Jonagold' and 'Fuji'.
*Time of fruit harvest.*—First day October 20th, last day October 30th, peak period October 25th to October 26th, at Morioka City, Iwate prefecture, Japan), same as 'Jonagold' and earlier than 'Fuji'.
*Amount of fruit harvest.*—30.3 kg per plant during a season.
*Time of fruit bearing.*—Precocious, same as 'Jonagold' and earlier than 'Fuji'.
*Self-fruitfulness* (*Fructification by self-pollination*).—None (0%), same as 'Fuji'.
*Early dropping of fruit.*—None or slight.
*Preharvest dropping of fruit.*—None or slight.

*Physiological disorder of fruit.*—Little, small cracking at stalk cavity.

*Keeping quality of fruit* (*room condition*).—Long (25 days), longer than 'Jonagold' and shorter than 'Fuji'.

*Storage quality of fruit* (*cold storage*) .—Long (70 days), same as 'Jonagold' and shorter than 'Fuji'.

*Occurrence of heart rot* (*Core rot*).—None or weak.

*Resistance to Alternaria blotch.*—Strong, same resistance as 'Jonagold' and stronger than 'Fuji'.

*Culture.*—As the new cultivar has tendency to form slightly small size of fruit, it is necessary to carry fruit thinning ahead of time, in order to accelerate enlargement of fruit. In addition, it is necessary to pay attention to optimum picking time and to avoid late picking, since storage quality of the present variety is inferior to that of 'Fuji'.

The new variety, 'Kotaro' is considered to be suitable in the main apple tree cultivating districts, especially in warm districts, as it is a high quality variety having good fruit appearance and excellent taste.

We claim:

1. A new and distinct cultivar of Apple tree, as illustrated and described.

* * * * *

Pedigree of 'Kotaro'